(12) United States Patent
Gangjee

(10) Patent No.: US 7,981,902 B2
(45) Date of Patent: Jul. 19, 2011

(54) SUBSTITUTED PYRROLO[2,3-D]PYRIMIDINES FOR SELECTIVELY TARGETING TUMOR CELLS WITH FR TYPE RECEPTORS

(75) Inventor: Aleem Gangjee, Allison Park, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 962 days.

(21) Appl. No.: 11/821,075

(22) Filed: Jun. 21, 2007

(65) Prior Publication Data
US 2008/0045710 A1 Feb. 21, 2008

Related U.S. Application Data

(60) Provisional application No. 60/817,065, filed on Jun. 28, 2006.

(51) Int. Cl.
C07D 487/04 (2006.01)
A61K 31/519 (2006.01)
A61P 35/04 (2006.01)

(52) U.S. Cl. ...................... 514/265.1; 544/280
(58) Field of Classification Search .................. 544/280; 514/265.1
See application file for complete search history.

(56) References Cited

U.S. PATENT DOCUMENTS
5,939,420 A 8/1999 Gangjee

FOREIGN PATENT DOCUMENTS
EP 0438261 A2 7/1991

OTHER PUBLICATIONS

Aleem Gangjee, Yibin Zeng, John J.L McGuire, and Roy L. Kisliuk, Synthesis of Classic Four-Carbon Bridged 5-Substituted Furo [2,3-d] pyrimidine and 6-Substituted Pyrrolo [2,3-d] pyrimid Analogues as Antifolates, J. Medical Chemistry 2005, pp. 5329-5336.

*Primary Examiner* — Susanna Moore
(74) *Attorney, Agent, or Firm* — Craig G. Cochenour; Buchanan Ingersoll & Rooney PC

(57) ABSTRACT

A compound for treating cancer tumors, particularly ovarian cancer tumors, is described, where a fused cyclic pyrimidine having a cancer treating ability is effective to allow selective delivery to a cancerous tumor.

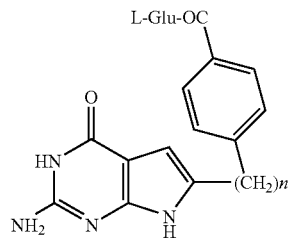

19 Claims, 1 Drawing Sheet

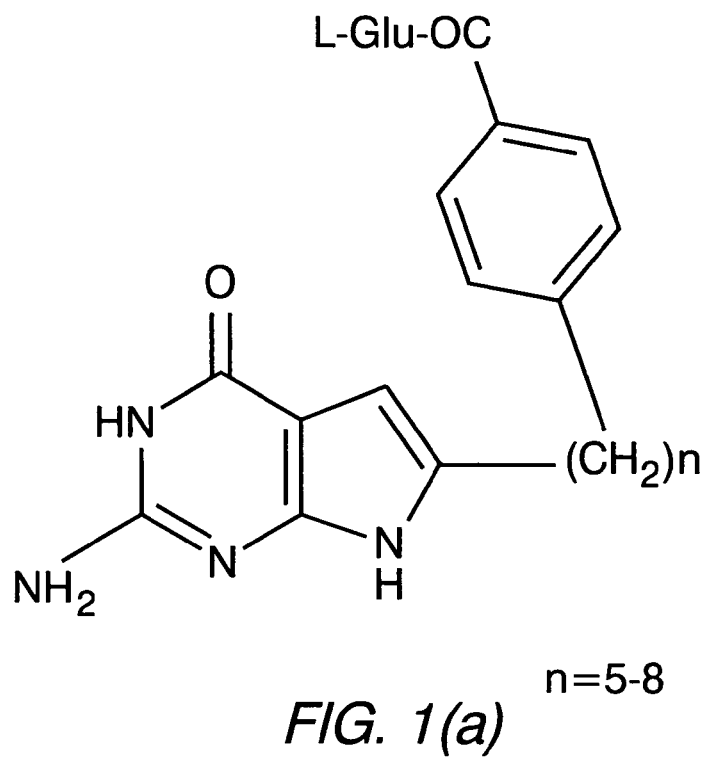
FIG. 1(a) n=5-8
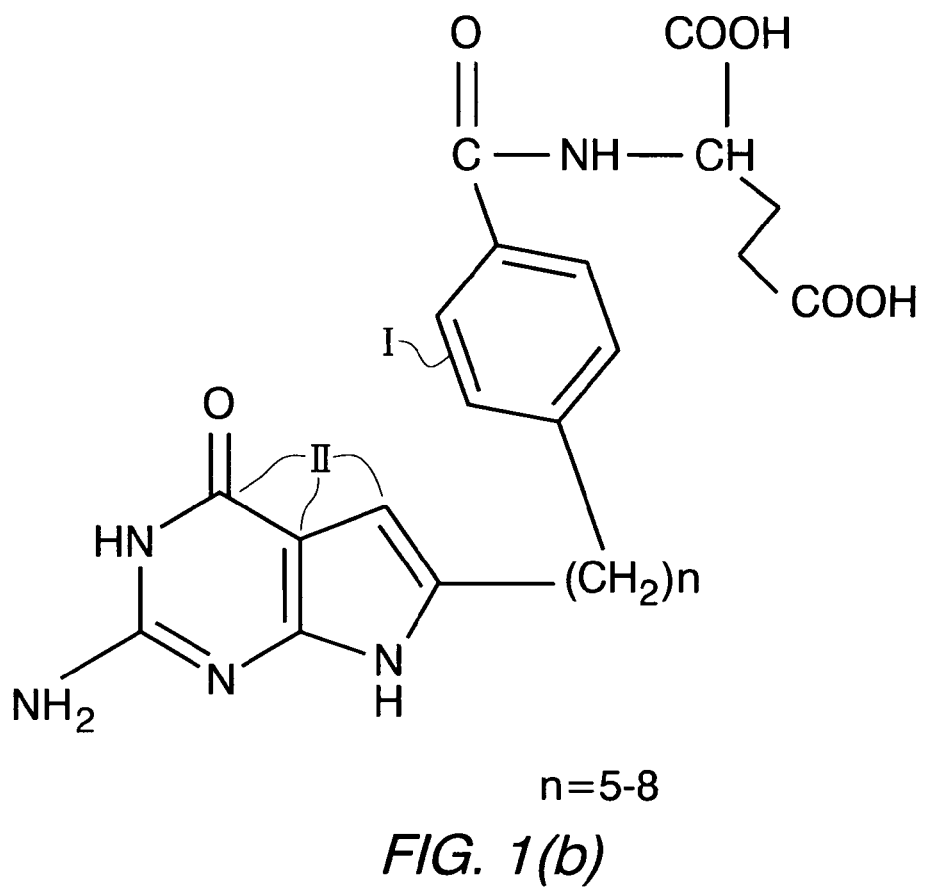
FIG. 1(b) n=5-8

SUBSTITUTED PYRROLO[2,3-D]PYRIMIDINES FOR SELECTIVELY TARGETING TUMOR CELLS WITH FR TYPE RECEPTORS

CROSS-REFERENCE TO RELATED APPLICATION

The instant application claims priority from U.S. Provisional Patent Application Ser. No. 60/817,065 filed Jun. 28, 2006, the disclosures of which are incorporated herein by reference.

GOVERNMENT CONTRACT

This invention was supported in part by the National Institutes of Health, U.S. Department of Health and Human Services under Contract No. CA 89300. The government has certain rights in the invention.

BACKGROUND OF THE INVENTION

1. Field of the Invention

The present invention relates to compounds that are selective chemotherapeutic agents which selectively target folate receptors (FR) of cancerous tumor cells and inhibit GARFTase contained in the cells, particularly types of ovarian cancer cells. Specifically, the present invention relates to fused cyclic pyrimidines, having a long chain $CH_2$ group between cyclic groups, which themselves selectively target folate receptors ("FR"), particularly FR-alpha of cancerous tumor cells. They also inhibit glycinamide ribonucleotide formyltransferace enzyme (GARFTase) in tumor cells, where the fused cyclic pyridimines themselves are effective to selectively penetrate inside of the cancerous tumor cells.

2. Description of the Prior Art

Cancer chemotherapy agents as taught, for example in U.S. Pat. No. 5,939,420 (Gangjee), do not specifically selectively target cancer tumor cells. However, chemotherapy agents have targeted both normal and tumor cells. This lack of selectivity for tumor cells results in cytotoxicity to the normal cells and is also one of the major causes of chemotherapeutic failure in the treatment of cancer. Further, advanced stage and platinum resistant tumors may be difficult to treat with traditional chemotherapeutic agents such as, but not limited to, carboplatin or paclitaxel (docitaxel). Other documents in this area include *J. Med. Chem.* 48 (16), 5329-5336, web release date Jul. 9, 2005 "Synthesis of Classical Four-Carbon Bridged 5-Substituted Furo-[2-3-d]-Pyrimidine and 6-Substituted Pyrrolo-[2,3-d]-Pyrimidine Analogues as Antifolates" by A. Gangjee et al.

As is known in the prior art, a type of folate receptor FR, FR-alpha, is overexpressed on a substantial amount of certain surfaces of a number of cancerous tumors including, but not limited to, ovarian, endometrial, kidney, lung, mesothelioma, breast, and brain tumors.

In most normal tissues, the FR-alpha is not present. In most normal tissues, folic acid is not taken up by normal cells by way of a reduced folate carrier system (RFC). In light of the specificity of the folic acid, conjugates of folic acid have been used in the prior art to selectively deliver toxins, liposomes, imaging and cytotoxic agents to FR-alpha expressing tumors.

However, one of the major limitations of the foregoing, such as cytotoxic-folic acid conjugates, is that this requires cleavage from the folic acid moiety to release the cytotoxic drug. Even more importantly, premature release of the cytotoxic agent during the transport before reaching the tumor destroys selectivity and thereby leads to undesired toxicity in normal cells. This is a very serious detriment scientifically and commercially.

Further, if the folic acid moiety of the cytotoxic-folic acid conjugate is difficult to cleave, then the anti-tumor activity is hindered as a result of the inability or reduced ability to release the cytotoxic agent. Accordingly, treatment of the tumor cells with the cytotoxic agent is either hindered or rendered nil as a result of the difficulty in cleaving the cytotoxic agent moiety from the folic acid-based conjugate.

In spite of the foregoing prior art, however, there remains a very real need for compositions that selectively target the FR of tumor cells.

An object of this invention is to provide compositions for selectively targeting FR, particularly FR-alpha, of tumor cells with a cancer-treating agent targeting the GARFTase enzyme.

In a related object, the compound does not contain conjugated compositions and does not need cleavage to release a cytotoxic drug.

In yet another related object, the compound will allow penetration into the cancerous cells expressing FR, that is, FR-alpha and/or FR-beta, but not into a cell using the reduced folate carrier system (RFC).

Another object of this invention is to provide a non-toxic FR targeting compound to the cancerous tumor in the process of treating a patient.

Another object of this invention is to efficiently target a cancerous tumor.

Another object of this invention is to utilize an essentially noncompound useful in treating a cancerous tumor.

SUMMARY OF THE INVENTION

The present invention has filled the above described need and satisfied the above objects by providing a narrow range of compounds that selectively target the FR of tumor cells. Other folate receptors of the FR-beta type are overexpressed on surfaces of myeloid leukemia cancerous tumors. The term "FR" used herein includes receptors selected from the group consisting of FR-alpha, FR-beta and mixtures thereof. In a preferred embodiment, the compositions selectively target FR-alpha and beta of cancerous tumor cells.

Very significantly, the cancer-treating compound is not significantly taken up by a cell or tissue using the RFC system.

The cancer-treating agent is a fused cyclic pyrimidine and is used to selectively target FR of ovarian tumors, advanced stage cancerous tumors that express FR receptors and drug-resistant tumors such as, but not limited to, those resistant to carboplatin, paclitaxel, and/or docitaxel. The receptors are preferably FR-alpha and beta types.

More specifically, the invention relates to a compound that is useful in inhibiting GARFTase in a cancerous tumor of a patient consisting essentially of: the fused cyclic pyrimidine shown in FIG. 1(a) and (b), where n=5-8 alkyl chain carbons between the major ring groups, I and II; wherein the compound is effective to selectively target a FR cancerous tumor, where due to the use of long chain carbons, n=5-8, the fused cyclic pyrimidine targets primarily cancerous tumors which contain FR to inhibit GARFTase within the tumors.

The distance and orientation of the side chain p-aminobenzoyl-L-glutamate moiety with respect to the pyrimide ring are extremely important for biological activity; hence, n=5-8 in FIGS. 1(a) and (b) provide surprisingly unique results. Here the fused cyclic pyrimidine acts as carrier, targeting and cancer treating agent. No conjugating of a separate cancer treating agent to the fused cyclic pyrimidine is required.

The invention will be more fully understood by review of the drawings in view of the following detailed description of the invention, and the claims appended thereto.

BRIEF DESCRIPTION OF THE DRAWINGS

FIG. 1(a) shows a general chemical formula for the fused cyclic pyrimide used in the method of this invention, where "L-Glu" is a L-Glutamic Acid (or L-Glutamate) group based on an amino acid having the formula $C_5H_9$—$NH_4$; and FIG. 1(b) shows another description of the formula of FIG. 1(a), where n is the total number of $CH_2$ groups between the major cyclic/ring groups, such groups shown as I and II.

DESCRIPTION OF THE PREFERRED EMBODIMENTS

As used herein, "tumor" refers to an abnormal growth of cells or tissues of the malignant type, unless otherwise specifically indicated and does not include a benign type tissue. The "tumor" may comprise of at least one cell and/or tissue. The term "inhibits or inhibiting" as used herein means reducing growth/replication. As used herein, the term "cancer" refers to any type of cancer, including ovarian cancer, leukemia, lung cancer, colon cancer, CNS cancer, melanoma, renal cancer, prostate cancer, breast cancer, and the like. As used herein, the term "patient" refers to members of the animal kingdom including but not limited to human beings. The fused cyclic pyrimidine of the invention has six unique properties: 1) inhibition of FR-alpha and beta cancerous tumors, 2) a lack of appreciable uptake by the RFC; 3) ability to act itself as a cancer treating agent; 4) ability to penetrate cancerous tumors having folate receptors; 5) ability to function as a substrate of folylpolyglutamate synthetase (FPGS) thereby being trapped in tumor cells; and 6) inhibition of GARFTase. The fused cyclic pyrimidine of this invention targets cancers with certain receptors, and is practically non-toxic. These fused cyclic pyrimidines are taken into the tumor cells.

Selectivity of the fused cyclic pyrimidine is made possible since most normal cells do not have FRs. FR-alpha is the most widely expressed receptor isoform in adult tissue. FR-alpha occurs at the apical (i.e., luminal) surface of epithelial cells where it is not supplied by folate in the circulation and does not take it up into the cell.

Embodiments of the invention follow. The fused cyclic pyrimidine where n=5-8 has a particular affinity for the receptors such as FR or FR-alpha or FR-beta which are mainly present on the surface of cancerous tumor cells and not other types of folate transport systems that are more predominant on the surface of normal cells. In other words, the fused cyclic pyrimidine of this invention having long chain $CH_2$ where n=5-8, preferably is not taken up to an appreciable degree by the reduce folate carrier (RFC) system. FR-alpha and beta receptors are generally not expressed in normal cells. The fused cyclic pyrimidine stays inside of the cancerous tumor cell for an adequate amount of time to kill the tumor cell. This occurs by way of polyglutamylation and the multi ionic form of the fused cyclic pyrimidine itself inside of the tumor cell. The fused cyclic pyrimidine also disrupts the replication process of the cancerous tumor cell, thereby inhibiting the growth of FR-alpha expressing cancerous tumor cells.

The foregoing embodiments are enabled by way of a glycinamide ribonucleotide formyltransferase ("GARFTase") inhibition. GARFTase is an enzyme which is essential to DNA synthesis of normal and cancerous tumor cells.

Here the fused cyclic pyrimidine itself has a high affinity for the FR-alpha receptors which are overexpressed on the surface of cancerous tumor cells. The fused cyclic pyrimidine passing into the cancerous tumor cells inhibits GARFTase activity and inhibits DNA synthesis. Accordingly, the targeted tumor cells which overexpress FR-alpha are prevented from replicating and are killed.

In a preferred embodiment, the fused cyclic pyrimidine has a significantly greater affinity for FR-alpha expressing cells compared with cells that do not express FR-alpha. Accordingly, the fused cyclic pyrimidine would have a greater affinity for cells which overexpress FR-alpha (i.e., certain cancerous tumor cells as described in more detail above) but also has an affinity for FR-beta cells.

At present, there appears to be no other agents known with the above-described six attributes in a single chemotherapy agent and therefore the presently invented compositions are unique with regard to other GARFTase or FR-alpha targeting agents, including any known agent in clinical or investigational use.

Moreover, other embodiments of the invention will be apparent to those skilled in the art from consideration of the specification and practice of the invention disclosed herein. It is intended that the specification be considered as exemplary only.

What is claimed is:

1. A compound effective in inhibiting glycinamide ribonucleotide formyltransferase (GARFTase) in cancerous tumors of a patient consisting essentially of a fused cyclic pyrimidine having the chemical formula:

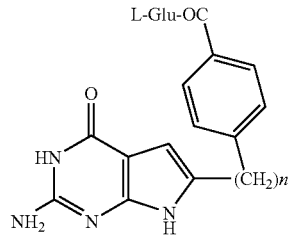

wherein n=5-8; and wherein the fused cyclic pyrimidine targets primarily folate receptors (FR) expressing cancerous tumors and itself acts as a cancer treating agent and inhibits GARFTase within the tumors.

2. The compound of claim 1 wherein n=5 in the chemical formula.

3. The compound of claim 1 wherein n=6 in the chemical formula.

4. The compound of claim 1 wherein n=7 in the chemical formula.

5. The compound of claim 1 wherein n=8 in the chemical formula.

6. A method for inhibiting glycinamide ribonucleotide formyltransferase (GARFTase) in cancerous tumors of a patient comprising:

(a) providing a fused cyclic pyrimidine having the chemical formula:

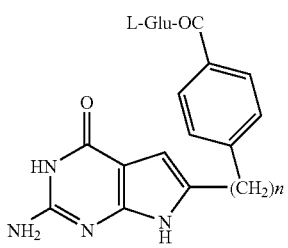

where n=7-8;
- (b) selectively delivering the fused cyclic pyrimidine alone to cancerous tumors, where the fused cyclic pyrimidine targets primarily folate receptor expressing (FR-expressing) cancerous tumors; and
- (c) effecting entry of said fused cyclic pyrimidine into said cancerous tumors where said fused cyclic pyrimidine itself acts as a cancer treating agent and inhibits GARFTase within the tumors.

7. The method of claim 6 including wherein said fused cyclic pyrimidine is selective for receptors selected from the group consisting of folate receptor alpha (FR-alpha), folate receptor beta (FR-beta), and mixtures thereof, associated with expressing cancerous tumors.

8. The method of claim 6 including wherein said fused cyclic pyrimidine is selective for folate receptor alpha (FR-alpha) expressing cancerous cells.

9. The method of claim 6 including wherein said fused cyclic pyrimidine is not significantly taken up by a tissue or a cell using the reduced folate carrier system (RFC system).

10. The method of claim 6 including wherein said fused cyclic pyrimidine functions as a substrate of folylpolyglutamate synthetase (FPGS) in the tumors, thereby being trapped in the tumors.

11. The method of claim 6 including wherein said fused cyclic pyrimidine stays inside the cancerous tumor for an effective amount of time to kill the tumors by way of polyglutamylation and the multi ionic form of the fused pyrimidine itself.

12. The method of claim 6 including wherein said fused cyclic pyrimidine requires no separate cancer treating agent or conjugation to a separate cytotoxic agent.

13. The method of claim 6 including wherein said fused cyclic pyrimidine targets at least one advanced stage cancerous tumor.

14. The method of claim 6 including wherein said fused cyclic pyrimidine targets at least one platinum resistant cancerous tumor.

15. The method of claim 6 including wherein said fused cyclic pyrimidine targets at least one carboplatin resistant cancerous tumor.

16. The method of claim 6 including wherein said fused cyclic pyrimidine targets at least one paclitaxel resistant cancerous tumor.

17. The method of claim 6 including wherein said fused cyclic pyrimidine targets at least one docitaxel resistant cancerous tumor.

18. The method of claim 6 including wherein said fused cyclic pyrimidine is polyglutamylated by folypoly-gamma glutamate synthetase.

19. The method of claim 6 including wherein said fused cyclic pyrimidine targets cancerous tumors selected from the group consisting of ovarian, endometrial, kidney, lung, mesothelioma, breast, and brain tumors.

* * * * *